(12) United States Patent
Woo et al.

(10) Patent No.: US 11,519,023 B2
(45) Date of Patent: Dec. 6, 2022

(54) PAPER-BASED COLORIMETRIC SENSOR KIT FOR QUICKLY AND SIMPLY DIAGNOSING MERCURY IN SITU WITH NAKED EYE AND METHOD FOR QUICKLY AND SIMPLY DETECTING MERCURY IN SITU WITH NAKED EYE USING THE SAME

(71) Applicant: KOREA FOOD RESEARCH INSTITUTE, Wanju-gun (KR)

(72) Inventors: Min-Ah Woo, Hwaseong-si (KR);
Min-Cheol Lim, Suwon-si (KR);
Sung-Wook Choi, Wanju-Gun (KR);
Tai-Yong Kim, Seongnam-si (KR)

(73) Assignee: KOREA FOOD RESEARCH INSTITUTE, Wanju-Gun (KR)

( * ) Notice: Subject to any disclaimer, the term of this patent is extended or adjusted under 35 U.S.C. 154(b) by 67 days.

(21) Appl. No.: 16/958,797

(22) PCT Filed: Dec. 27, 2018

(86) PCT No.: PCT/KR2018/016758
§ 371 (c)(1),
(2) Date: Jun. 29, 2020

(87) PCT Pub. No.: WO2019/132543
PCT Pub. Date: Jul. 4, 2019

(65) Prior Publication Data
US 2021/0062252 A1    Mar. 4, 2021

(30) Foreign Application Priority Data

Dec. 27, 2017 (KR) .................. 10-2017-0181402

(51) Int. Cl.
*C12Q 1/6853* (2018.01)
*G01N 21/25* (2006.01)

(52) U.S. Cl.
CPC ......... *C12Q 1/6853* (2013.01); *G01N 21/251* (2013.01); *C12Q 2525/307* (2013.01);
(Continued)

(58) Field of Classification Search
CPC ............ C12Q 1/6853; C12Q 2531/125; C12Q 2563/155
See application file for complete search history.

(56) References Cited

U.S. PATENT DOCUMENTS

2006/0068433 A1 *   3/2006   Godfrey ................. C12Q 1/686
435/6.18

FOREIGN PATENT DOCUMENTS

| KR | 10-2009-0070860 | 7/2009 |
| KR | 10-2012-0018549 | 3/2012 |

OTHER PUBLICATIONS

Kim et al. Nanomaterials 2018; 8: 81, doi:10.3390/nano8020081. (Year: 2018).*

(Continued)

*Primary Examiner* — Angela M. Bertagna
(74) *Attorney, Agent, or Firm* — Lex IP Meister, PLLC

(57) ABSTRACT

There is provided a paper-based colorimetric sensor kit for quickly and simply diagnosing mercury in situ with a naked eye. The paper-based colorimetric sensor kit includes: a circular template for rolling circle amplification (RCA); a primer that does not hybridize to the circular template when a mercury ion is bonded to a primer that hybridizes to the circular template; a DNA polymerase; a sensing material kit including a nanoparticle probe labeled to a DNA coil formed in the circular template for RCA; and a radial chromatography paper.

9 Claims, 12 Drawing Sheets

Specification includes a Sequence Listing.

(52) U.S. Cl.
CPC .. *C12Q 2531/125* (2013.01); *C12Q 2563/155* (2013.01); *C12Q 2565/137* (2013.01)

(56) References Cited

OTHER PUBLICATIONS

Lv et al. Analyst 2017; 142: 4708 (Year: 2017).*
Zhou et al. Analytica Chimica Acta 2012; 713: 45-49 (Year: 2012).*
Wang et al. Microchimica Acta 2016; 183: 2855-2860 (Year: 2016).*
Xing et al. Analyst 2013; 138: 3457-3462 (Year: 2013).*
Jin Lv et al., "Highly Effective Target Converting Strategy for Ultrasensitive Electrochemical Assay of Hg2+", Analyst, vol. 142, No. 24, pp. 4708-4714, Nov. 8, 2017. DOI: 10.1039/C7AN01306J.
Guan-Hua Chen et al., "Detection of mercury (II) ions using colorimetric gold nanoparticles on paper-based analytical devices", Analytical Chemistry, vol. 86, No. 14, Jun. 16, 2014.
Jinfeng Chen et al., "Highly sensitive fluorescent sensor for mercury based on hyperbranched rolling circle amplification", Analyst, vol. 140, No. 3, pp. 907-911, Dec. 8, 2014. DOI: 10.1039/c4an01769b.

\* cited by examiner

Au NP probes only

Au NP probes + RCA product

SEQUENCE LISTING

```
<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: Primer

<400> SEQUENCE: 1
tttttttttt tt                                                           12

<210> SEQ ID NO 2
<211> LENGTH: 54
<212> TYPE: DNA
<213> ORGANISM: Artificial Sequence
<220> FEATURE:
<223> OTHER INFORMATION: ssDNA

<400> SEQUENCE: 2
gtcctcagtc ccaatagaag cggagcttca aaaaaaaaaa aacgtctgaa gagg             54

<210> SEQ ID NO 3
<211> LENGTH: 12
<212> TYPE: DNA
<213> ORGANISM: Artificial Sequence
<220> FEATURE:
<223> OTHER INFORMATION: Primer

<400> SEQUENCE: 3
aactcggaga ac                                                           12

<210> SEQ ID NO 4
<211> LENGTH: 54
<212> TYPE: DNA
<213> ORGANISM: Artificial Sequence
<220> FEATURE:
<223> OTHER INFORMATION: circular template phosphate

<400> SEQUENCE: 4
gtcctcagtc ccaatagaag cggagcttca gttctccgag ttcgtctgaa gagg             54
```

PAPER-BASED COLORIMETRIC SENSOR KIT FOR QUICKLY AND SIMPLY DIAGNOSING MERCURY IN SITU WITH NAKED EYE AND METHOD FOR QUICKLY AND SIMPLY DETECTING MERCURY IN SITU WITH NAKED EYE USING THE SAME

TECHNICAL FIELD

The present disclosure relates to a sensor for diagnosing a mercury ion in water and a method for detecting a mercury ion in water using the same, and more particularly, to a paper-based colorimetric sensor kit for quickly and simply diagnosing a mercury ion in water in situ with a naked eye and a method for quickly and simply detecting a mercury ion in situ with a naked eye using the same.

BACKGROUND ART

Mercury is one of toxic heavy metal materials that may seriously threaten the global environment and human health. In particular, a mercury ion ($Hg^{2+}$) is one of the most important factors of water pollution. The mercury ion ($Hg^{2+}$) is converted into methyl mercury through a microbial biosynthetic pathway, and the methyl mercury is easily absorbed into a bacteria, plankton, and fish. This causes serious damage to a brain, a nervous system, a kidney, and an endocrine system of a human.

Recently, examples of a most common method used for detecting mercury include inductively coupled plasma mass spectrometry (ICP-MS), atomic absorption spectroscopy (AAS), and gas chromatography (GC). In these methods, a wide range of metal ions may be detected with high sensitivity and selectivity, but an expensive and sophisticated device and a skilled person are required. In addition, it takes a lot of time for detection, and a labor-intensive procedure is required. Accordingly, the development of a method capable of quickly and simply implementing detection immediately in situ with a naked eye is required.

DISCLOSURE

Technical Problem

The present invention has been made in an effort to provide a paper-based colorimetric sensor kit for detecting mercury having advantages of quickly and simply sensing mercury in situ in real time with a naked eye with no complicated and expensive measuring device, and a method for quickly and simply detecting mercury in situ with a naked eye using the same.

Exemplary embodiments according to the present invention may be used to achieve other objects which are not mentioned in detail in addition to the objects.

Technical Solution

An exemplary embodiment of the present invention provides a paper-based colorimetric sensor kit for quickly and simply diagnosing mercury in situ with a naked eye, the paper-based colorimetric sensor kit including: a circular template for rolling circle amplification (RCA); a primer that hybridizes to the circular template and does not hybridize to the circular template when a mercury ion is bonded thereto; a DNA polymerase; a sensing material kit including a nanoparticle probe labeled to a DNA coil formed in the circular template for RCA; and a radial chromatography paper.

Another exemplary embodiment of the present invention provides a method for quickly and simply diagnosing mercury in situ with naked eye, the method including: mixing and reacting a detection solution with a primer that hybridizes to a circular template for rolling circle amplification (RCA) and does not hybridize to the circular template when a mercury ion is bonded thereto; mixing the circular template for RCA, a DNA polymerase, a nanoparticle probe labeled to a DNA coil formed in the circular template for RCA, and dNTP in the mixed reaction solution to perform an RCA reaction; adding the solution in which the RCA reaction is completed dropwise to a radial chromatography paper and then drying the solution; and observing concentric circles formed on the radial chromatography paper.

Advantageous Effects

When the paper-based colorimetric sensor kit according to the present disclosure is used, a concentration of the mercury ion ($Hg^{2+}$) may be easily measured without being affected by lighting conditions such as weather, sunlight intensity, and an angle at a reading point through the very simple and robust measurement by using a portable spectrophotometer. That is, when the paper-based colorimetric sensing method according to an exemplary embodiment of the present invention is used, since the concentration of the mercury ion ($Hg^{2+}$) may be determined without a bulky and expensive tool for reading, and a simple, portable, and cost effective approach is provided, a quick and simple diagnosis in situ with a naked eye may be available.

MODE FOR INVENTION

Figure 1:
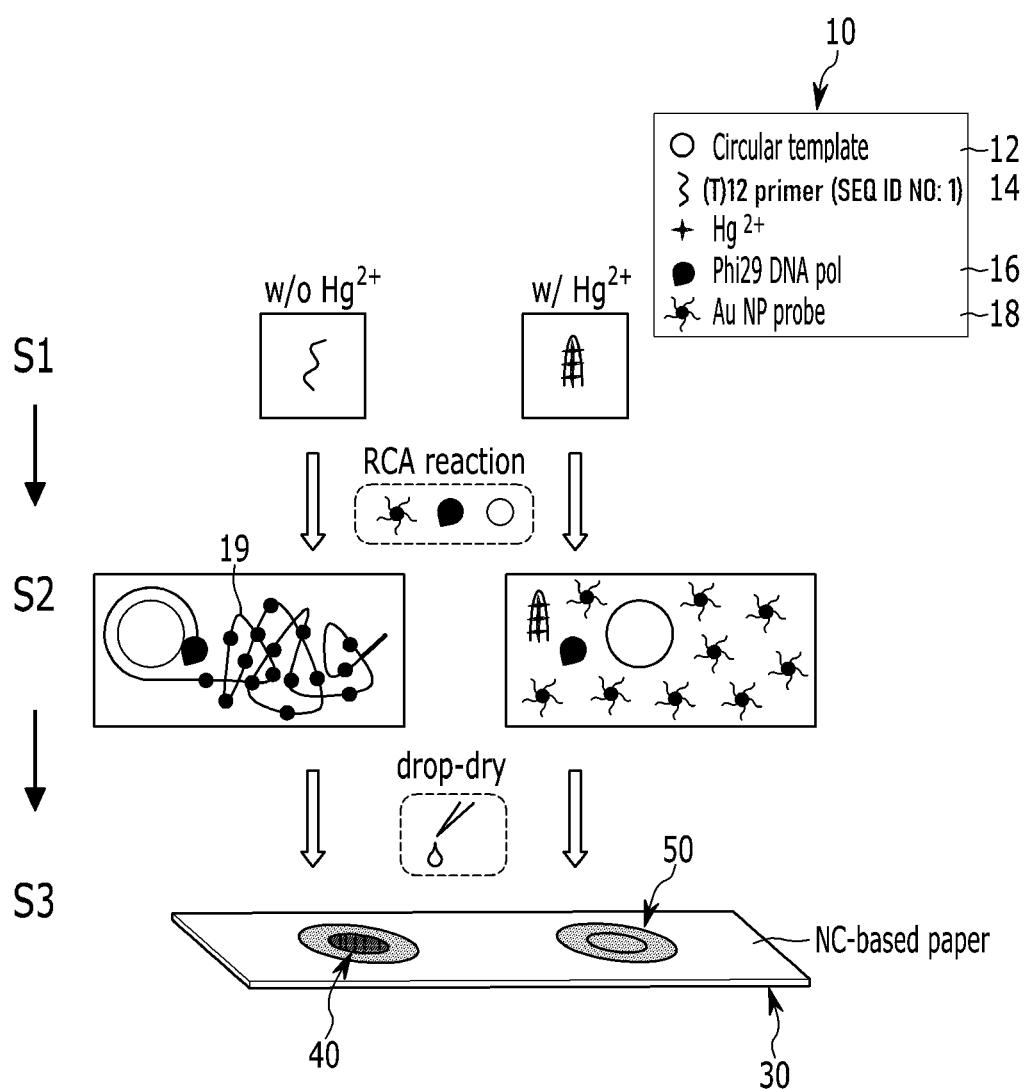
FIG. 1 is a conceptual view showing a method for simply detecting mercury in situ with a naked eye using a paper-based colorimetric sensor kit according to an exemplary embodiment of the present invention.

Hereinafter, exemplary embodiments of the present invention will be described in detail with reference to the accompanying drawings so that those skilled in the art to which the present invention pertains may easily practice the present invention. The present invention may be implemented in various different forms and is not limited to the exemplary embodiments described herein.

Throughout the present specification, unless explicitly described to the contrary, the word "comprising" any components will be understood to imply the inclusion of other components rather than the exclusion of any other components. In the drawings, a size and a thickness of each component are randomly represented for convenience of explanation, and the present invention is not limited thereto.

FIG. 1 is a conceptual view showing a method for simply detecting mercury in situ with a naked eye using a paper-based colorimetric sensor kit according to an exemplary embodiment of the present invention.

The paper-based colorimetric sensor kit according to an exemplary embodiment of the present invention includes a sensing material kit for detecting a mercury ion ($Hg^{2+}$) and paper for a colorimetric reaction.

A sensing material kit 10 includes a circular template 12 for rolling circle amplification (RCA), a primer 14, a DNA polymerase 16, and a nanoparticle probe 18.

First, in order to test the presence or absence of the mercury ion, a test object and the primer 14 are reacted with each other (S1).

When the test object is in a solution state like tap water, the test object is mixed in a reactor containing the sensing material kit 10. When the test object is not a solution, a sampled test object is dissolved in distilled water and then the test object is mixed in the reactor containing the sensing material kit 10.

The reaction of the primer 14 with the test object may be performed at room temperature at 10 to 30 minutes.

Subsequently, an RCA reaction is performed (S2). For the RCA reaction, the circular template 12, the DNA polymerase 16, the nanoparticle probe 18, and dNTP are mixed in a reactor containing a solution in which the test object and the primer are mixed and the mixture is incubated at 30° C. for 30 to 60 minutes, and then the RCA reaction may be performed.

RCA is an isothermal enzymatic process mediated by a specific DNA polymerase in which a long ssDNA molecule is synthesized in a short circular ssDNA template by using one DNA primer. Since a single strand DNA coil formed of a DNA concatemer that is spatially condensed and has a micron size detectable with an amplified single molecule in RCA, RCA is a powerful sensing system. In several general RCA detection sensors, the RCA reaction is induced by connection of padlock probes depending on the presence of a detection object.

On the other hand, in an exemplary embodiment of the present invention, a selective reaction of the primer 14 to the mercury ion ($Hg^{2+}$) is used. When the primer 14 is in a normal state, the primer 14 hybridizes to the circular template 12 for RCA. However, when the mercury ion ($Hg^{2+}$) is present, the mercury ion ($Hg^{2+}$) is bonded to the primer 14 to inhibit bonding of the primer 14 to the circular template 12.

The circular template 12 for RCA is a template in which a single strand DNA (ssDNA) of about 50 to 80 bp is formed in a circular shape.

In a case where the mercury ion ($Hg^{2+}$) is absent, when the primer 14 in a normal state is hybridized to the circular template 12, the RCA reaction is induced by the DNA polymerase (for example, Phi29 DNA Polymerase) 16.

A single strand DNA coil 19 formed of a DNA concatemer having a micron size is formed under an isothermal condition during the RCA reaction. The nanoparticle probe 18 is labeled to the single strand DNA coil 19 formed as described above.

On the other hand, when the mercury ion ($Hg^{2+}$) is present, the mercury ion ($Hg^{2+}$) is bonded to the primer 14 to inhibit hybridization of the primer 14 to the circular template 12. For example, in a case where the primer 14 is thymine oligonucleotide, the mercury ion ($Hg^{2+}$) is bonded to the thymine oligonucleotide, and a thymine-$Hg^{2+}$-thymine coordination bond is thus formed, which leads to conversion of the primer into a double strand complex. Therefore, the primer 14 may not be hybridized to the circular template 12.

The nanoparticle probe 18 may be formed of oligonucleotide capable of hybridizing to the single strand DNA coil 19 and a nanoparticle (NP) exhibiting a predetermined color. For example, the NP may be an Au NP, and the oligonucleotide may be functionalized to the Au NP by using streptavidin-biotin.

When the RCA completed solution is added dropwise onto a radial chromatography paper 30 and the solution is dried, a color change on the paper may be quickly and simply measured within a few seconds by using a portable spectrophotometer (S3).

In the radial chromatography paper 30, a solution to be measured in a radial manner, rather than in a lateral manner is dropped to the center of the radial chromatography paper 30 and a principle that fluidity is changed depending on a size and a weight of a molecule is used, such that the presence or absence and a degree of the mercury ion ($Hg^{2+}$) may be easily confirmed.

A resolution may vary depending on a material, pore size, hydrophilicity, or hydrophobicity of the radial chromatography paper 30. The radial chromatography paper 30 may be a chromatography paper formed of polyvinylidene fluoride (PVDF), nitrocellulose (NC), and the like.

When the solution in which the RCA reaction is completed is added dropwise to the radial chromatography paper 30, the reaction solution moves from the center of the paper toward an edge of the paper based on a capillary action. Components of the solution are separated into a radial shape in a mobile phase, spots of compounds different each other are formed into rings of concentric circles in a stationary phase. Amounts of the DNA coil and the Au NP probe complex in a detection system vary depending on a concentration of the mercury ion ($Hg^{2+}$). When the mercury ion ($Hg^{2+}$) is absent or the concentration of the mercury ion ($Hg^{2+}$) is low, a color intensity of a central spot 40 of the concentric circle is high. On the other hand, when the concentration of the mercury ion ($Hg^{2+}$) is high, the RCA reaction is inhibited, and Au NP thus freely spreads away in a radial direction. As a result, a color intensity of an outer circle 50 of the concentric circle is high. Accordingly, the color intensity of each central spot 40 may be quantified by using a portable spectrophotometer.

The following experimental examples and drawings are provided to better understand the conceptual aspects and methods of the exemplary embodiments of the present invention and to describe actions and effects of the exemplary embodiments of the present invention. However, the experimental examples are set forth to illustrate the present invention, and the scope of the present invention is not limited thereto.

EXPERIMENTAL EXAMPLE

Preparation of Circular Template

Figure 2:
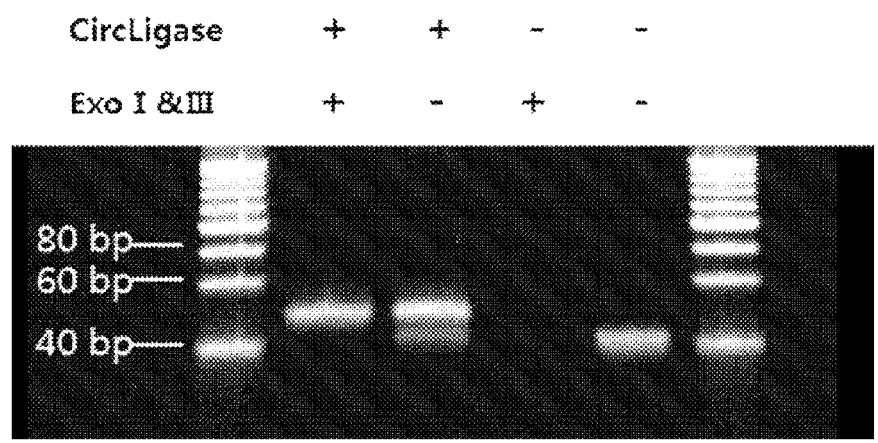
FIG. 2 illustrates a PAGE analysis result for confirming the presence or absence of a formation of a circular template.

For synthesis of a circular template ssDNA, 100 μL of a reaction mixture solution (4 μL of 100 U/μL DNA ligase, 10 μL of reaction buffer solution, 71 μL of distilled water (DDW), 5 μL of 1 mM ATP, and 5 μL of 50 mM $MnCl_2$) containing 5 μl of 100 μM linear ssDNA (5'-phosphate GTCCTCAGTCCCAATAGAAGCGGAGCTTCAAAAA-AAAAAAAACGTCTGAAGAGG-3') (SEQ ID NO: 2) having a length of 54 bp was connected at 60° C. for 8 hours, and then was inactivated at 80° C. for 10 minutes. Then, in order to eliminate a remaining linear ssDNA, 6 μL of a 20 U/μL exonuclease I and 3 μL of a 10 U/μL exonuclease III were added thereto and then incubated at 37° C. for 4 hours and then at 80° C. for 20 minutes. After a product was purified by using an oligo clean-up and concentration kit, and was confirmed by 15% modified urea-polyacrylamide gel electrophoresis (PAGE) at 100 V for 75 minutes with a 1×TBE buffer solution, and then gel staining was performed with a 1×SYBR Green II for 15 minutes. The results are illustrated in FIG. 2.

Preparation of Au NP Probe

In order to prepare an Au NP probe, a surface of an Au NP conjugated with streptavidin (SA-Au NP) was functionalized with biotinylated oligonucleotide. A shape of the Au NP was observed at an acceleration voltage of 80 kV with a transmission electron microscope (TEM).

Specifically, an SA-Au NP solution (300 μL, 10 OD) was mixed with a 100 μM biotinylated ssDNA probe (5'-TTTTTTTTTTTT (SEQ ID NO: 1)-C6SP-biotin). Then, the mixture was subjected to shaking incubation at room temperature (18 to 23° C.) for 3 hours and then was shaken and incubated and incubated at 4° C. over all night. In order to obtain a purified DNA probe modified into an Au NP, the solution was washed three times through centrifugation in 6000×g for 30 minutes, and then was re-suspended in a 1x PB buffer solution having a pH of 7.5. The mixture was washed twice with distilled water. The shape of the Au NP probe was observed with the TEM.

Figure 3:
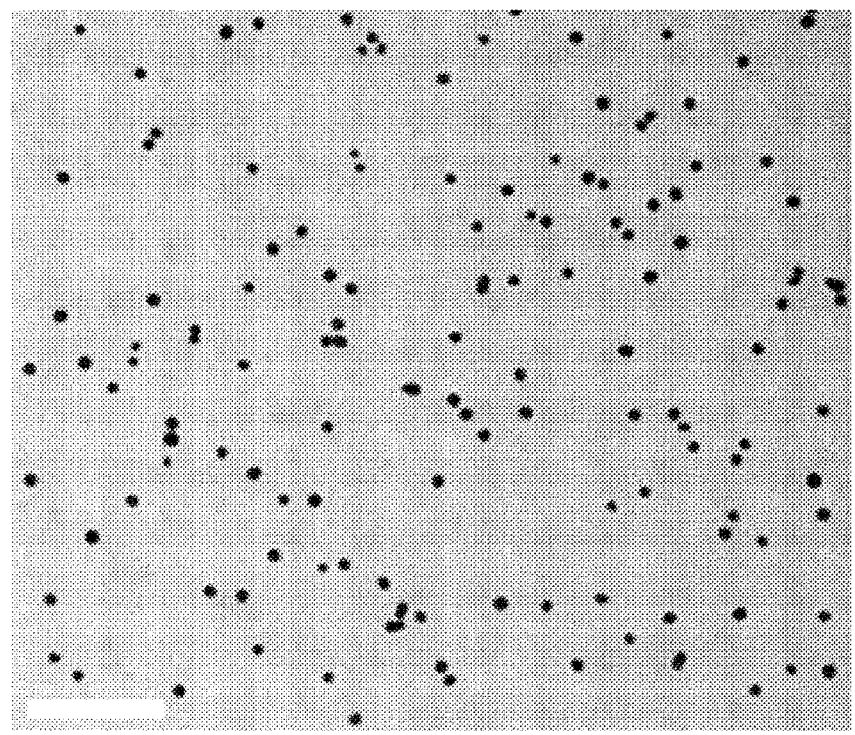
FIG. 3 is a transmission electron microscope (TEM) photograph in a case where only an Au NP probe is present.
Figure 4:
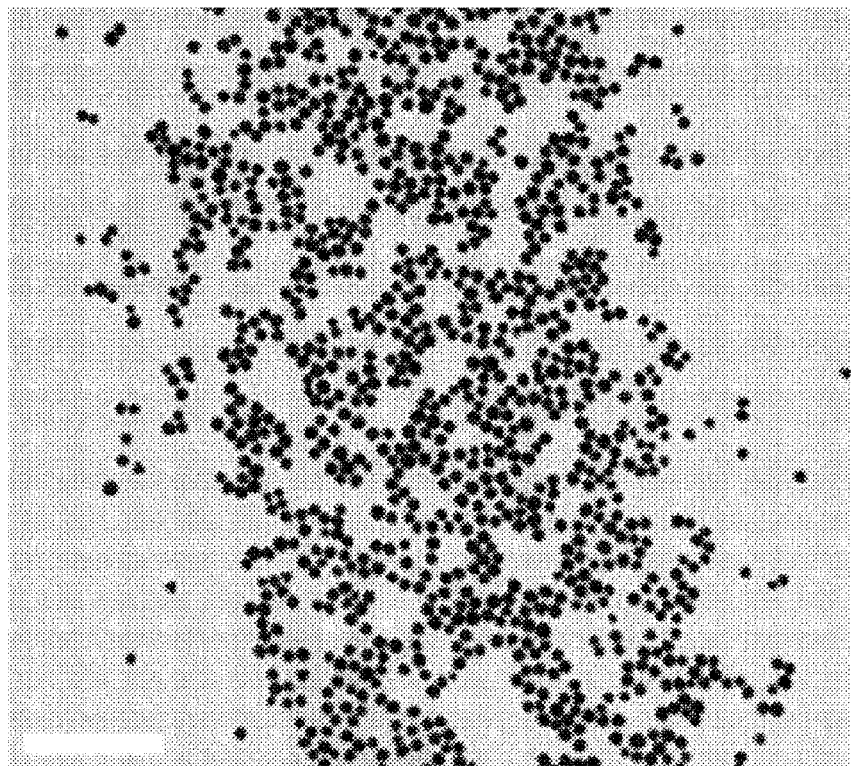
FIG. 4 is a TEM photograph showing a state in which Au NP probes are aggregated by being labeled to a single strand (ssDNA) coil.

As illustrated in FIG. 3, the Au NP probes are dispersed well in the solution and have a circular shape. On the contrary, as illustrated in FIG. 4, an aggregation phenomenon of the Au NP probes is observed when a hybridization reaction of the Au NP probe and the ssDNA coil is performed. This is interpreted to be because the oligonucleotide of the Au NP probe is complementarily bonded to the ssDNA coil.

Figure 5:
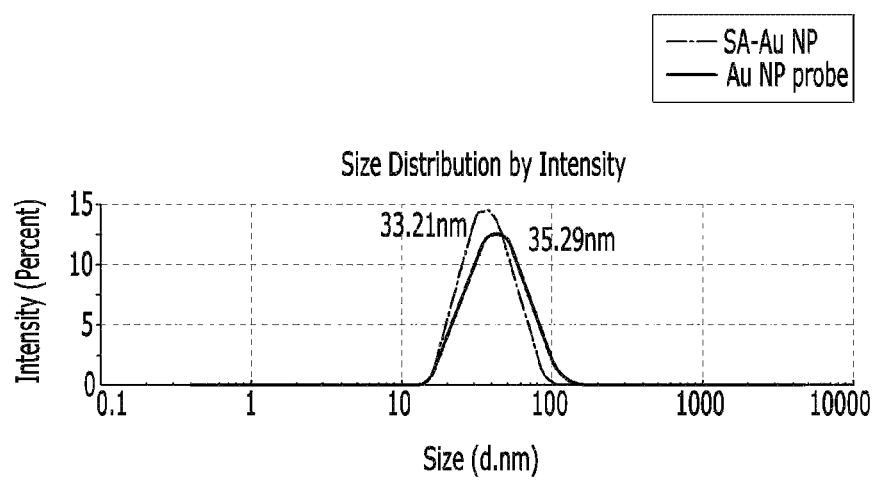
FIG. 5 illustrates a result of measuring characteristics of the Au NP probe by dynamic light scattering.
Figure 6:
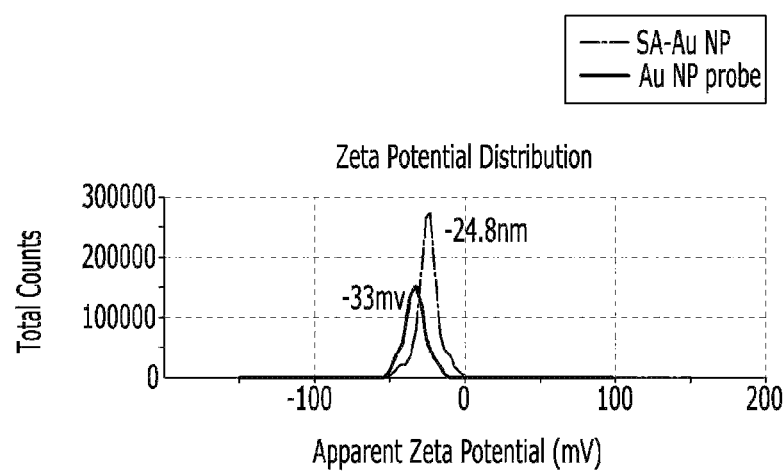
FIG. 6 illustrates a result of measuring the characteristics of the Au NP probe by a zeta potential.

Results of measuring characteristics of the Au NP probe by dynamic light scattering (DLS) and a zeta potential are illustrated in FIGS. 5 and 6. After biotinylated oligonucleotide negatively charged was introduced onto a surface of the SA-Au NP, it can be appreciated that a size and a surface charge of the Au probe were changed. It can be appreciated that an average diameter of particles was changed from 33.21 nm to 35.29 nm as illustrated in FIG. 5, and a negative charge was increased from −24.8 mV to −33.8 mV as illustrated in FIG. 6. These results show that the oligonucleotide was successfully attached to the surface of the SA-Au NP, and further stabilization was achieved by a non-specific aggregation due to the increased negative surface charge.

RCA Reaction Test By Using Circular Template-(T)12 SEQ ID NO: 1) Primer Complex

A test was carried out to confirm DNA amplification through a formation of a circular template-(T)12 (SEQ ID NO: 1) primer complex. The circular template-(T)12 (SEQ ID NO: 1) primer complex having various concentrations was tested under a test condition of the RCA reaction, and a SYBR Green II was used as a staining reagent for determining an amount of the amplified ssDNA coil.

Specifically, a fluorescence intensity of the SYBR Green II after the RCA reaction was measured in order to confirm the amount of the ssDNA coil according to an amount of the circular template-(T)12 (SEQ ID NO: 1) primer complex.

First, 80 μL of a total reaction mixture (10×8 μL of buffer, 7.5 μL of 10 MM dNTP, 3 μL of 25 U/μL phi29 DNA polymerase, and 41.5 μL of DDW) containing the circular template-(T)12 (SEQ ID NO: 1) primer complex having various concentrations (6, 3, 1.5, 0.75, 0.375, and 0 μM) was reacted at 30° C. for 90 minutes, and then was inactivated at 65° C. for 10 minutes. Then, 1 μL of a 100×SYBR Green II was added thereto and was incubated at room temperature for 30 minutes, and then the fluorescence intensity of the SYBR Green II was measured with a multi-mode microplate reader (SpectraMax i3x, Molecular Devices, Sunnyvale, Calif., USA).

Figure 7:
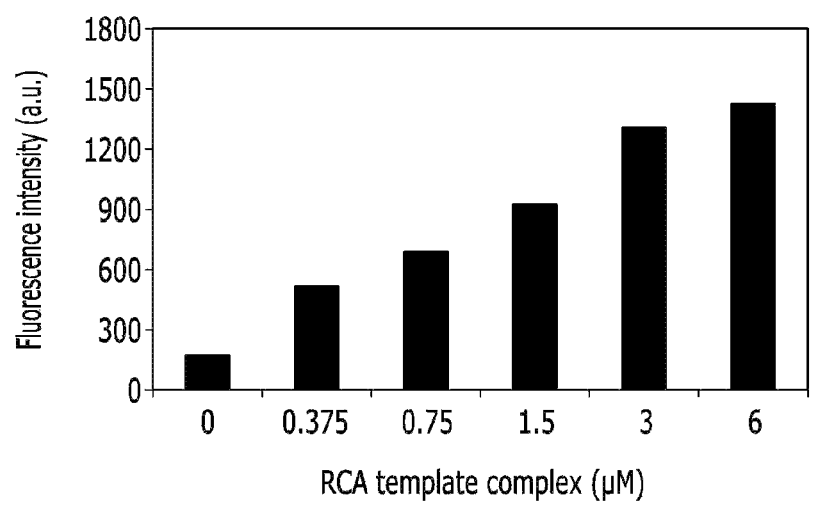
FIG. 7 illustrates a synthesis yield of the ssDNA coil according to an amount of a circular template-(T)12 (SEQ ID NO: 1) primer complex.

FIG. 7 illustrates a yield of the ssDNA coil according to the amount of the circular template-(T)12 primer (SEQ ID NO: 1) complex. As the amount of the circular template-(T)12 primer (SEQ ID NO: 1) complex was increased from 0 to 6 μM, the fluorescence intensity of the SYBR Green II was also increased. This result shows that the circular oligonucleotide successfully acts as a template for RCA and the amount of the ssDNA coil formed by RCA is in proportion to the amount of the circular template-(T)12 (SEQ ID NO: 1) primer complex.

Selectivity to Mercury in Paper-Based Colorimetric Sensing Method

Figure 8:
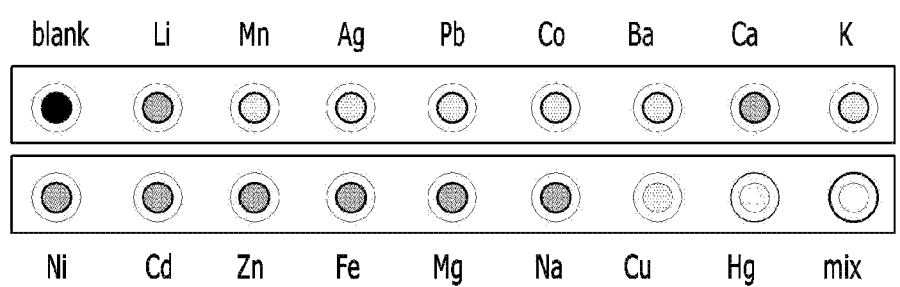
FIG. 8 illustrates a digital image of rings of concentric circles formed on paper after a reaction of metal ions different from each other with a primer.

In order to confirm selectivity to the mercury ion ($Hg^{2+}$) in the suggested analysis method, the mercury ion ($Hg^{2+}$) and various metal ions were tested three times, a solution was dropped to an NC film and dried, and then colorimetric intensities of central spots were compared with each other. The results are illustrated in FIG. 8. A final concentration of each metal ion was 1 μM.

Specifically, in order to evaluate the selectivity to the mercury ion, 16 metal ions ($Li^+$, $Mn^{2+}$, $Ag^+$, $Pb^{2+}$, $Co^{2+}$, $Ba^{2+}$, $Ca^{2+}$, $K^+$, $Ni^{2+}$, $Cd^{2+}$, $Zn^{2+}$, $Fe^{2+}$, $Mg^{2+}$, $Na^+$, $Cu^{2+}$, and $Hg^{2+}$) were tested. First, 5 μL of a 200 nM (T)12 primer (SEQ ID NO: 1) solution was mixed with 5 μL of each of 16 μM_metal ions or 5 μL of a metal ion mixture, and then the mixture was incubated at room temperature for 30 minutes. Then, an RCA reaction mixture [10 μL of 150 nM circular template, 8 μL of 10 x reaction buffer solution, 7 μL of 10 mM dNTP, 2.5 μL of 10 U/μL phi29 DNA polypolymerase, 12.5 μL of DDW, and Au NP probe (3.3 OD)] was added thereto and then was incubated at 30° C. for 30 minutes and at 65° C. for 10 minutes. Subsequently, 10 μL of each reaction solution was added dropwise onto the NC film and then dried. The results were analyzed by using a portable spectrophotometer (RM200QC, X-Rite Co., Neu-Isenburg, Germany).

The spectrophotometer uses CIE L* a* b* (CIELAB) representing a color space designated by Commission Internationale del'Eclairage (CIE). CIELAB represents all colors visible to the human eye and is provided as an independent model of a device to be used for reference. When the color is represented in CIELAB, L* is defined as brightness, a* represents a red/green value, and b* represents a yellow/blue value. A value of ΔE represents a color difference calculated by the following equation.

$$\Delta E=[(\Delta L^*)2+(\Delta a^*)2+(\Delta b^*)2]^{1/2}$$

Figure 9:
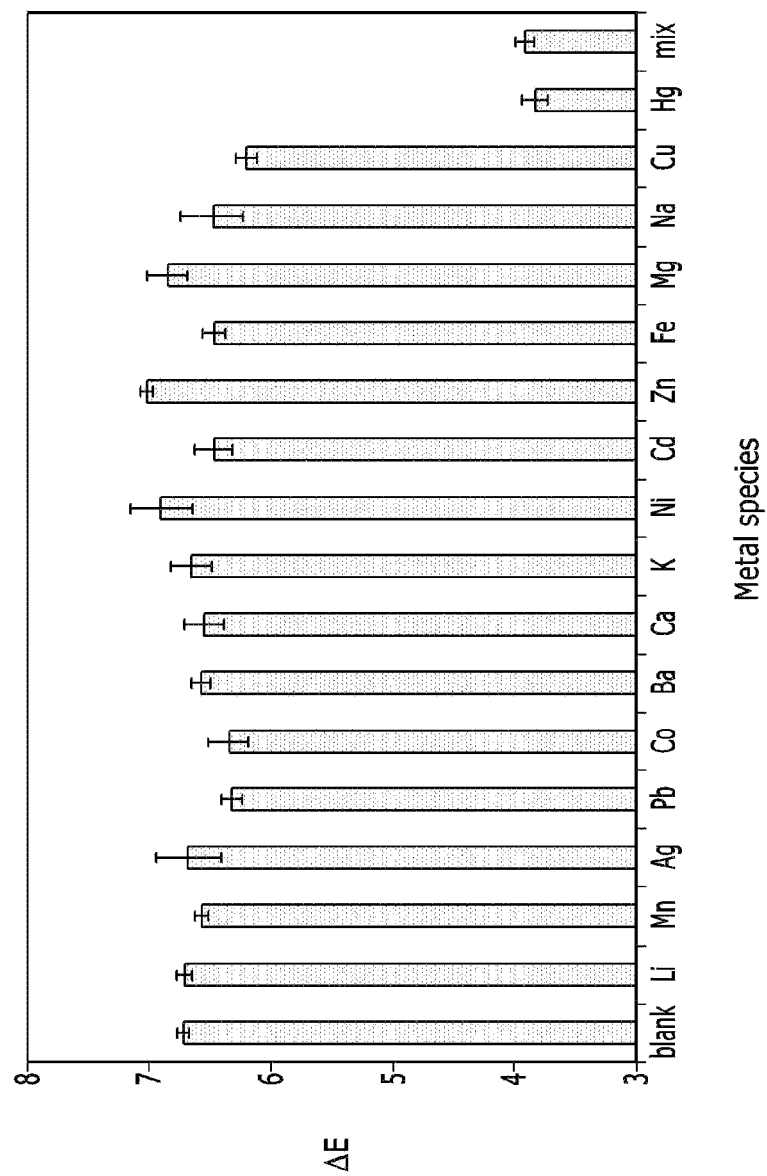
FIG. 9 illustrates a bar graph showing a color intensity (ΔE) quantified by a portable spectrophotometer.

FIG. 8 illustrates a digital image of the central spots and the rings of the concentric circles formed on the paper. FIG. 9 illustrates a bar graph of a color intensity (ΔE) quantified by a portable spectrophotometer. Color concentrations of the central spots on the paper could be easily distinguished with a naked eye, and could be numerically measured by using the portable spectrophotometer. In addition, it can be appreciated that the color concentration may be constantly measured regardless of an exterior lighting condition because the portable spectrophotometer comes completely in contact with the paper at the time of measuring the color concentrations of the central spots on the paper. This function shows the advantage as a sensor for detecting a mercury ion ($Hg^{2+}$) in situ.

As illustrated in FIG. 8, the color concentrations of the internal central spots were low in only two samples of a sample including only the mercury ion ($Hg^{2+}$) and a mixture including the mercury ion ($Hg^{2+}$). This shows that RCA is inhibited by the mercury ion ($Hg^{2+}$). Meanwhile, in a case of a metal ion sample other than the mercury ion ($Hg^{2+}$), the color intensity of the central spot was further high due to bonding of the Au NP to the DNA coil. These results demonstrate that the suggested analysis method is selective to the mercury ion ($Hg^{2+}$).

Figure 10:
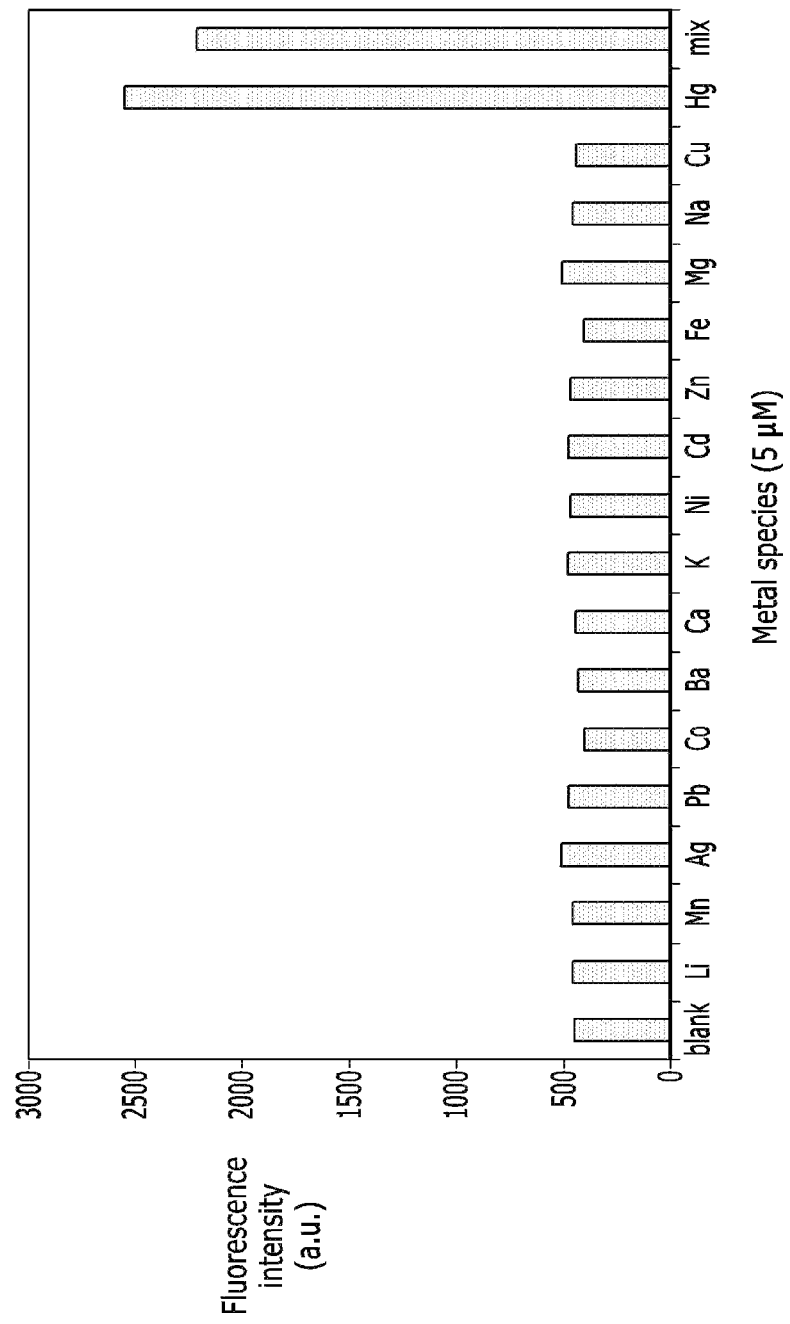
FIG. 10 illustrates a fluorescence intensity graph showing a result of measuring selectivities of the primer to the metal ions different from each other.

In addition, a selectivity of the (T)12 primer (SEQ ID NO: 1) to the mercury ion ($Hg^{2+}$) is illustrated in FIG. 10. When comparing values of the metal ion samples having the same concentrations with each other, a high fluorescence value of the SYBR Green I was exhibited only in the sample including only the mercury ion ($Hg^{2+}$) and the mixture including the mercury ion ($Hg^{2+}$). This is because the single strand primer was converted into a double strand complex due to a thymine-$Hg^{2+}$-thymine coordination bond.

Figure 11:
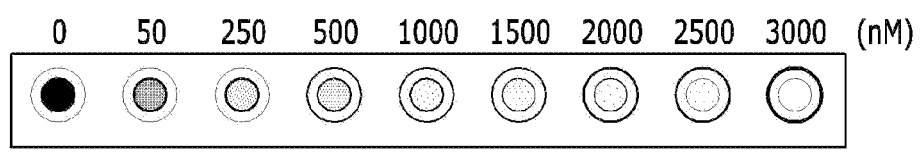
FIG. 11 is a digital image showing a colorimetric reaction on paper to mercury ion concentrations different from each other.

Quantization of Mercury Ion ($Hq^{2+}$) Using Paper-Based Colorimetric Sensing Method FIG. 11 is a digital image after a solution is dropped onto the NC paper and dried. Referring to FIG. 11, it can be appreciated that in a case where the mercury ion ($Hg^{2+}$) was absent, a deep red spot appeared at the center of the concentric circle, and as the concentration of the mercury ion ($Hg^{2+}$) was increased, the color intensity was reduced. On the contrary, it can be appreciated that the color intensity of each of edge rings of the concentric circles was increased as the concentration of the mercury ($Hg^{2+}$) was increased.

Figure 12:
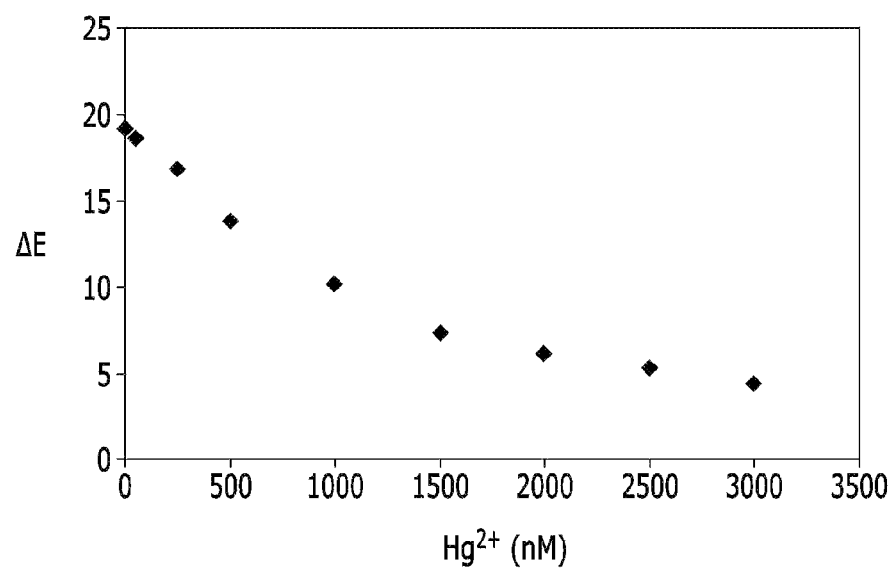
FIG. 12 illustrates a graph showing a color intensity (ΔE) obtained by measuring a colorimetric reaction according to nine mercury ion concentrations different from each other by using a spectrophotometer.
Figure 13:
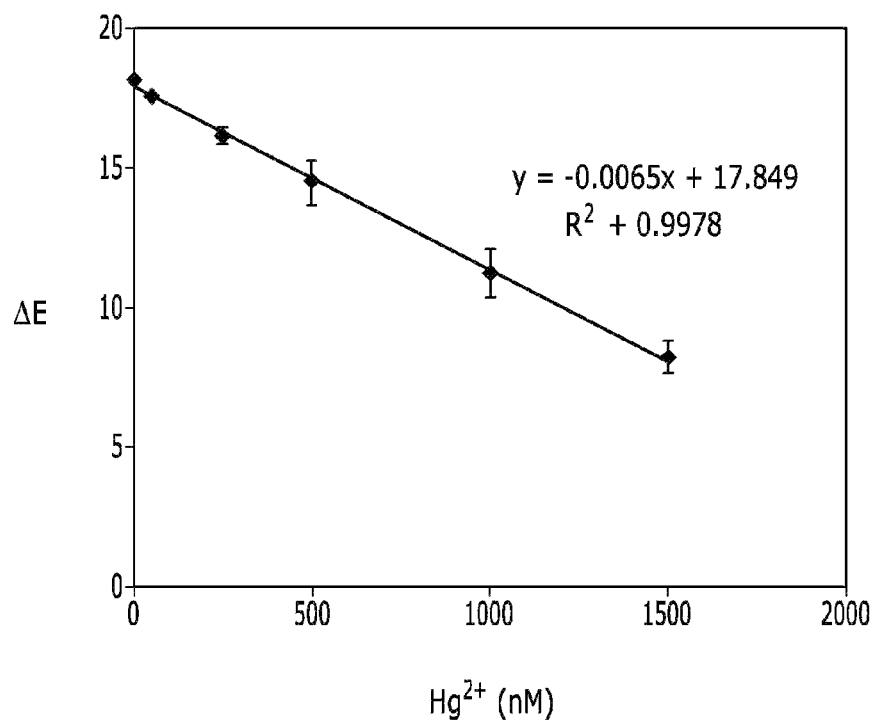
FIG. 13 illustrates a graph showing a colorimetric reaction according to six mercury ion concentrations different from each other, the colorimetric reaction quantified by using a spectrophotometer.

The results of quantifying the red spots of the concentric circles by using the portable spectrophotometer are illustrated in FIGS. 12 and 13. FIG. 12 illustrates results of measuring nine samples having various concentrations (0, 50, 250, 500, 1,000, 1,500, 2,000, 2,500, and 3,000 nM) of the mercury ion ($Hg^{2+}$). The measured color concentrations (ΔE) of the central spots of the concentric circles on the paper were 19.2, 18.6, 16.8, 13.8, 10.2, 7.3, 6.1, 5.3, and 4.4, respectively, the value of ΔE was likely to be reduced as the concentration of the mercury ion ($Hg^{2+}$) was increased.

FIG. 13 illustrates results of the measurement performed at a concentration of the mercury ion ($Hg^{2+}$) ranging from 0 to 1,500 nM. Six samples having the different concentrations (0, 50, 250, 500, 1,000, and 1,500 nM) of the mercury ion ($Hg^{2+}$) were tested three times, and then an average value thereof is illustrated in FIG. 13. Referring to FIG. 13, the average values of ΔE were 18.1±0.05, 17.5±0, 16.1±0.25, 14.4±0.77, 11.2±0.86, and 8.2±0.57. A linear curve for a concentration range of the mercury ion ($Hg^{2+}$) from 0 to 1,500 nM and the value of ΔE was obtained, a detection limit of the mercury ion ($Hg^{2+}$) at a signal-to-noise ratio of 3 was calculated as 21.8 nM (n=3). A few seconds was enough to perform the measurement using the portable spectrophotometer. Accordingly, it can be appreciated that since a total analysis time including the RCA reaction and the measurement is about 90 minutes, the measurement may be very quickly and simply performed.

Detection of Mercury Ion ($Hq^{2+}$) in Tap Water

In order to demonstrate applicability of the present detection method in a real sample, the mercury ion ($Hg^{2+}$) was added to tap water while changing the concentration of the mercury ion ($Hg^{2+}$) to 0, 50, 250, 500, 1,000, and 1,500 nM, and then three samples were tested for each concentration by using the paper-based colorimetric sensing method. Before mixing of the mercury, the tap water was prepared after being filtered through an NC syringe filter membrane having a pore size of 0.22 μm.

Figure 14:
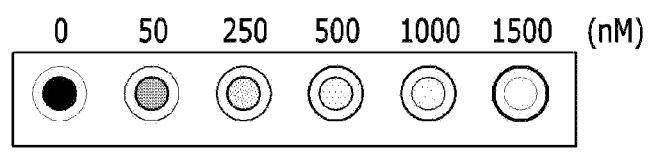
FIG. 14 is a digital image obtained by measuring a colorimetric reaction on paper after addition of mercury ions ($Hg^{2+}$) to tap water while changing a concentration of the mercury ion to 0, 50, 250, 500, 1,000, and 1,500 nM.
Figure 15:
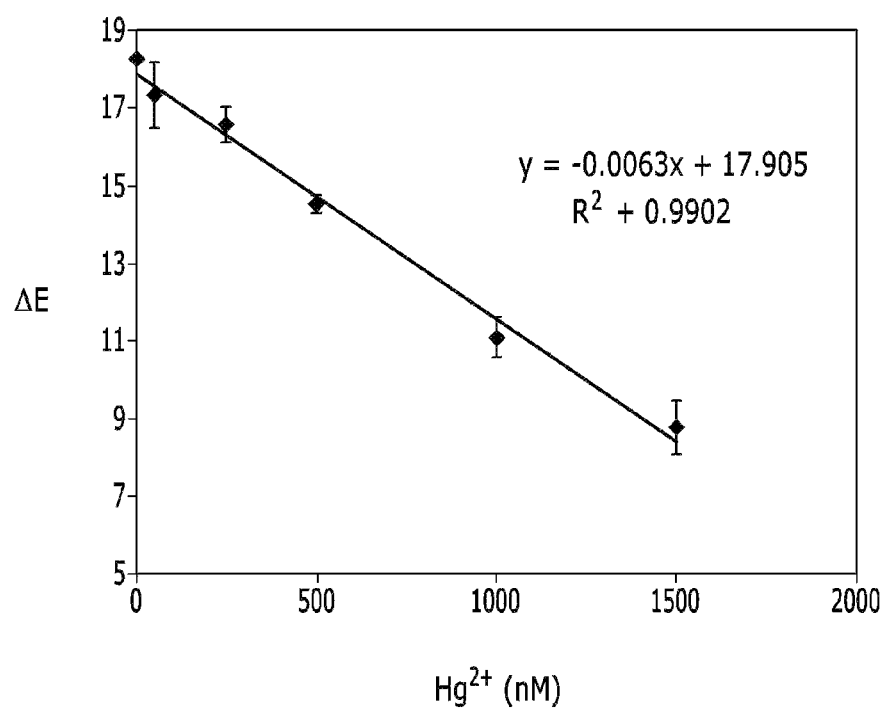
FIG. 15 illustrates a graph showing a colorimetric reaction on paper quantified by using a spectrophotometer after addition of mercury ions ($Hg^{2+}$) to tap water while changing a concentration of the mercury ion to 0, 50, 250, 500, 1,000, and 1,500 nM.

The colorimetric test results are illustrated in FIGS. 14 and 15. The average values of ΔE measured for each of the concentrations of 0, 50, 250, 500, 1,000, and 1,500 nM of the mercury ion ($Hg^{2+}$) were 18.27±0.05, 17.33±0.83, 16.57±0.48, 14.5±0.22, 11.07±0.52, and 8.77±0.68, respectively. The linear curve of the values of ΔE was obtained in a range of 0 to 1,500 nM $Hg^{2+}$, and the detection limit at a signal-to-noise ratio of 3 was calculated as 22.4 nM (n=3).

Measurement of Selectivity of (T)12 (SEQ ID NO: 1) Primer

After a complex including a control primer (5'-AACTCG-GAGAAC-3') (SEQ ID NO: 3) having another base sequence instead of the (T)12 (SEQ ID NO: 1 primer was formed, a selectivity to mercury was measured.

Figure 16:
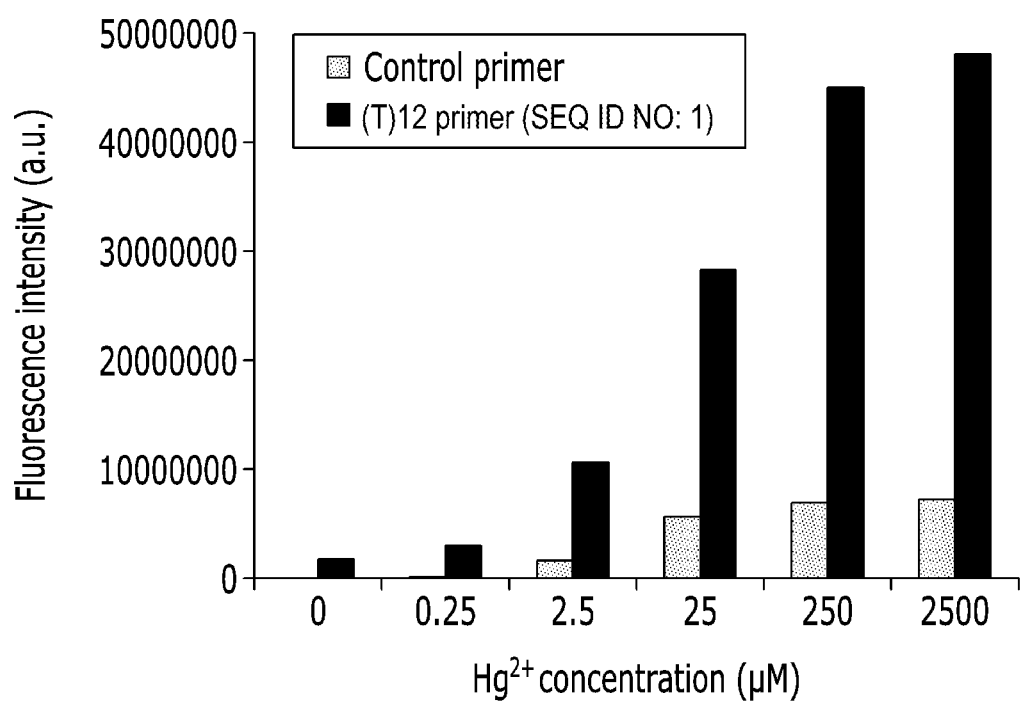
FIG. 16 illustrates a result of measuring SYBRI fluorescence values according to a concentration of a mercury ion ($Hg^{2\pm}$) in a case of using a (T)12 (SEQ ID NO: 1) primer according to an exemplary example and in a case of using a control primer.
Figure 17:
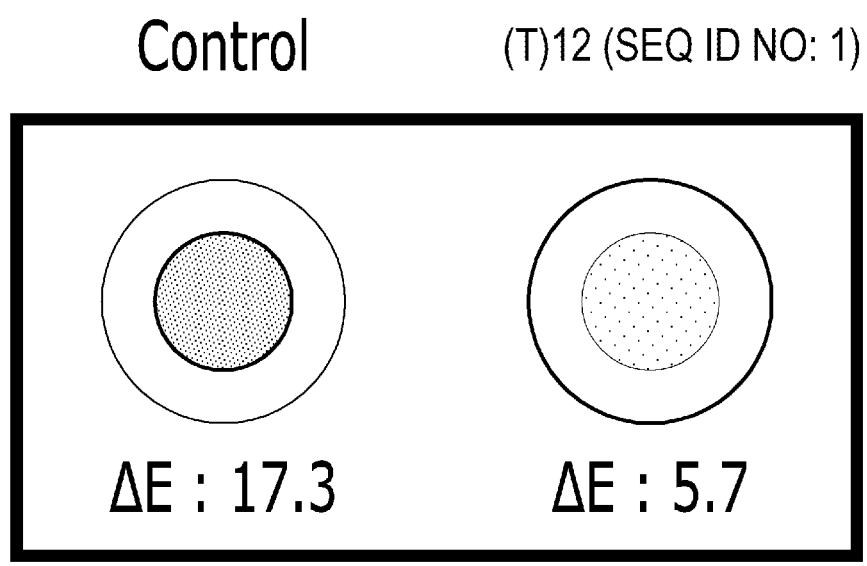
FIG. 17 is a digital image obtained by measuring a colorimetric reaction after an RCA reaction with respect to each of a circular template-(T)12 (SEQ ID NO: 1) primer complex according to an exemplary example and a control group (circular template-control primer).

As illustrated in FIG. 16, the fact that the SYBRI fluorescence value of the (T)12 (SEQ ID NO: 1) primer is increased as compared to that of the control primer as the mercury concentration is increased is the result of a T-Hg-T coordination bond between the T(12) (SEQ ID NO: 1)

primer and mercury. As illustrated in FIG. 17, it could be confirmed that in a case where the control primer and the circular template (5'-phosphate GTCCTCAGTCC-CAATAGAAGCG-GAGCTTCAGTTCTCCGAGTTCGTCTGAAGAGG-3') (SEQ ID NO: 4) prepared to be complementarily bonded thereto were used, a deep red was exhibited at the central spot due to a normal RCA reaction, but in a case where the T(12) (SEQ ID NO: 1) primer was used, the color was hardly exhibited at the central spot due to inhibition of the RCA reaction.

As described above, when the paper-based colorimetric sensing method according to an exemplary embodiment of the present invention is used, the concentration of the mercury ion ($Hg^{2+}$) may be easily measured without being affected by lighting conditions such as weather, sunlight intensity, and an angle at a reading point through the very simple and robust measurement by using the portable spectrophotometer. That is, when the paper-based colorimetric sensing method according to an exemplary embodiment of the present invention is used, since the concentration of the mercury ion ($Hg^{2+}$) may be determined without a bulky and expensive tool for reading, and a simple, portable, and cost effective approach is provided, a quick and simple in situ diagnosis with a naked eye may be possible.

Although the preferred exemplary embodiments of the present invention have been described above, the present invention is not limited thereto, and various modifications can be made and carried out within the scope of the claims and the detailed description of the invention, and also belong to the scope of the present invention.

INDUSTRIAL APPLICABILITY

The present invention may be applied to a quick and simple diagnosis of mercury in situ with a naked eye.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

The invention claimed is:

1. A paper-based colorimetric sensor kit for quickly and simply detecting a mercury ion in situ with a naked eye, the paper-based colorimetric sensor kit comprising:
 a circular template for rolling circle amplification (RCA);
 a primer that hybridizes to the circular template and does not hybridize to the circular template when a mercury ion is bonded to the primer;
 a DNA polymerase;
 a sensing material kit including a nanoparticle probe attached to a single-stranded oligonucleotide that is capable of hybridizing to a single-stranded DNA coil formed from the circular template when the circular template is amplified by RCA; and
 radial chromatography paper.

2. The paper-based colorimetric sensor kit of claim 1, wherein the primer is a thymine oligonucleotide.

3. The paper-based colorimetric sensor kit of claim 1, wherein the nanoparticle probe is an Au nanoparticle probe.

4. The paper-based colorimetric sensor kit of claim 3, wherein the Au nanoparticle probe is obtained by binding biotinylated oligonucleotide to a streptavidin-functionalized Au nanoparticle probe.

5. A method for quickly and simply detecting a mercury ion in situ with a naked eye, the method comprising:
 mixing and reacting a detection solution with a primer that hybridizes to a circular template for rolling circle amplification (RCA) and does not hybridize to the circular template when a mercury ion is bonded to the primer;
 mixing the circular template for RCA, a DNA polymerase, a nanoparticle probe attached to a single-stranded oligonucleotide that is capable of hybridizing to a single-stranded DNA coil formed from the circular template when the circular template is amplified by RCA, and dNTP in the mixed solution to perform an RCA reaction;
 adding the solution in which the RCA reaction is completed dropwise to a radial chromatography paper and then drying the solution; and
 observing concentric circles formed on the radial chromatography paper.

6. The method of claim 5, wherein the primer is a thymine oligonucleotide.

7. The method of claim 5, wherein the nanoparticle probe is an Au nanoparticle probe.

8. The method of claim 7, wherein the Au nanoparticle probe is obtained by binding biotinylated oligonucleotide to a streptavidin-functionalized Au nanoparticle probe.

9. The method of claim 5, wherein the observing of the concentric circles formed on the radial chromatography paper includes calculating a concentration of the mercury ion depending on a color intensity of a central spot of the concentric circle by using a portable spectrophotometer.

\* \* \* \* \*